(12) United States Patent
Li et al.

(10) Patent No.: US 10,661,032 B2
(45) Date of Patent: May 26, 2020

(54) LIQUID TANK, ATOMIZER AND ELECTRONIC CIGARETTE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Renjin Wu, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 328 days.

(21) Appl. No.: 15/630,827

(22) Filed: Jun. 22, 2017

(65) Prior Publication Data
US 2017/0281883 A1    Oct. 5, 2017

(30) Foreign Application Priority Data

Jun. 22, 2016  (CN) ..................... 2016 2 0621899 U

(51) Int. Cl.
| A24F 47/00 | (2020.01) |
| A61M 15/06 | (2006.01) |
| A61M 15/00 | (2006.01) |
| A61M 11/04 | (2006.01) |

(52) U.S. Cl.
CPC ......... *A61M 11/041* (2013.01); *A24F 47/006* (2013.01); *A61M 11/042* (2014.02); *A61M 15/0001* (2014.02); *A61M 15/06* (2013.01)

(58) Field of Classification Search
CPC ..... A24F 47/008; A61M 15/00; A61M 15/06; A61M 15/0001; A61M 15/0021; A61M 11/00; A61M 11/04; A61M 11/042

USPC ......................................... 131/270, 273, 194
See application file for complete search history.

(56) References Cited

U.S. PATENT DOCUMENTS

| 10,433,580 B2 * | 10/2019 | Kobal .................. A24B 15/303 |
| 2014/0048086 A1 * | 2/2014 | Zhanghua ............ A24F 47/008 131/329 |
| 2014/0299137 A1 * | 10/2014 | Kieckbusch .......... A24F 47/008 131/328 |
| 2015/0020826 A1 * | 1/2015 | Liu ....................... A24F 47/008 131/329 |
| 2016/0100633 A1 * | 4/2016 | Gao ...................... A24F 47/008 131/329 |

* cited by examiner

*Primary Examiner* — Bradley H Philips
*Assistant Examiner* — Savannah L Gabriel
(74) *Attorney, Agent, or Firm* — Cheng-Ju Chiang

(57) ABSTRACT

An exemplary liquid tank for an atomizer includes a bottom part, a liquid outlet, a first air inlet, a first porous liquid blocking element, and a top part. The bottom part has a first end and an opposite second end, and defines a liquid chamber for containing tobacco liquid. The liquid outlet is defined in the second end. The first air inlet is defined in the first end, so that external air can enter the liquid chamber via the first air inlet. The first porous liquid blocking element covers the first air inlet. The first porous liquid blocking element is capable of preventing the tobacco liquid in the liquid chamber from flowing out via the first air inlet, and allows air to pass through. The top part is detachably connected to the first end. The top part and the bottom part cooperatively clamp the first liquid blocking element therebetween.

11 Claims, 6 Drawing Sheets

LIQUID TANK, ATOMIZER AND ELECTRONIC CIGARETTE HAVING SAME

TECHNICAL FIELD

The present invention relates to electronic cigarettes, and particularly to a liquid tank, an atomizer, and an electronic cigarette using same.

BACKGROUND ART

A typical atomizer includes an atomizing unit, and a liquid tank connected to the atomizing unit. The liquid tank defines a liquid outlet at an end connecting with the atomizing unit. Tobacco liquid stored in the liquid tank flows into the atomizing unit via the liquid outlet, so that the atomizing unit atomizes the tobacco liquid.

However, external air goes into the liquid tank also through the liquid outlet. Accordingly, a negative pressure may exist in the liquid tank, and thus, the tobacco liquid may flow out unsmoothly. Therefore, an atomization effect of the atomizer may be unsatisfactory.

What are needed, therefore, are a liquid tank, an atomizer, and an electronic cigarette using same, which can overcome the above shortcomings.

SUMMARY

An exemplary liquid tank for an atomizer includes a bottom part, a liquid outlet, a first air inlet, a first porous liquid blocking element, and a top part. The bottom part has a first end and an opposite second end, and defines a liquid chamber for containing tobacco liquid. The liquid outlet is defined in the second end. The first air inlet is defined in the first end, so that external air can enter the liquid chamber via the first air inlet. The first porous liquid blocking element covers the first air inlet. The first porous liquid blocking element is capable of preventing the tobacco liquid in the liquid chamber from flowing out via the first air inlet, and allows air to pass through. The top part is detachably connected to the first end. The top part and the bottom part cooperatively clamp the first liquid blocking element therebetween.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
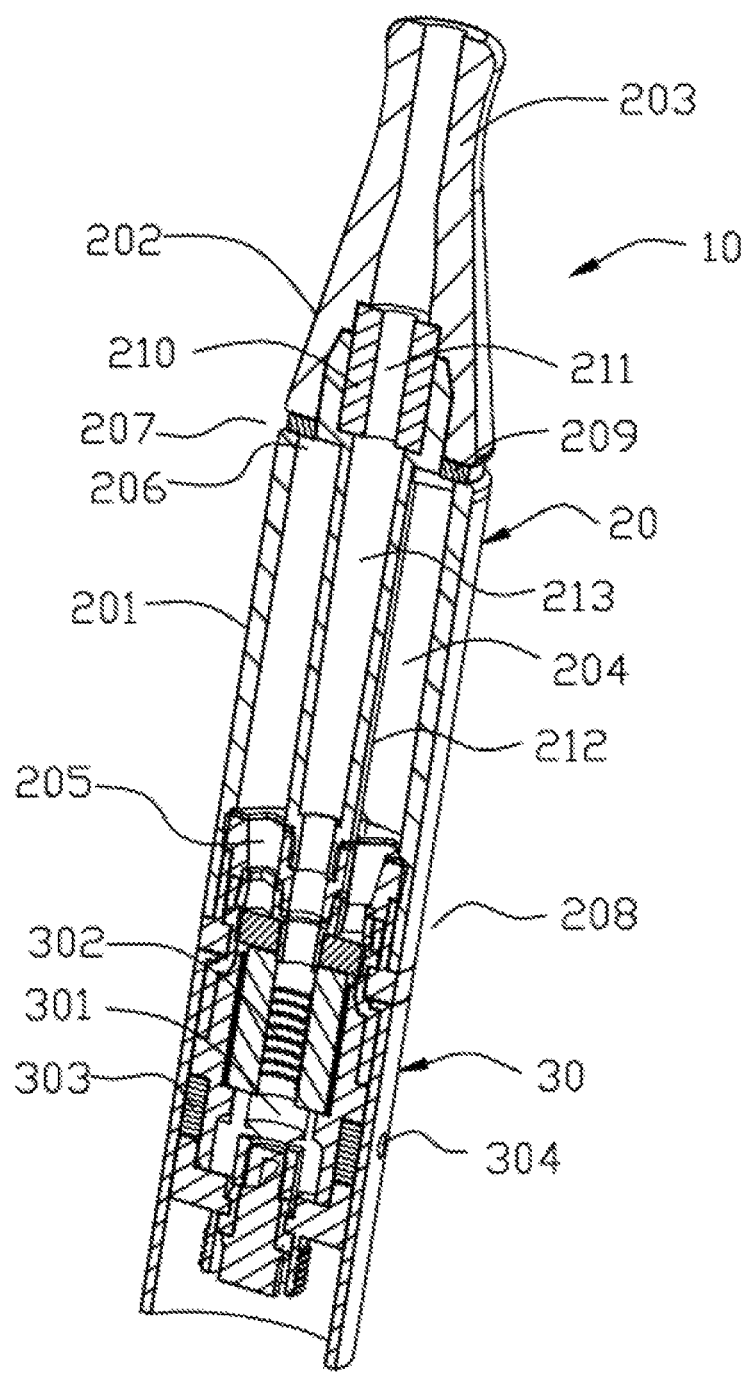
FIG. 1 is a cut-off perspective view of an atomizer according to a first embodiment, including a liquid tank.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Referring to FIG. 1, an atomizer 10 is shown. The atomizer 10 includes a liquid tank 20 and an atomizing unit 30. The liquid tank 20 includes a first end 207 and an opposite second end 208. The atomizing unit 30 is connected to the second end 208. The atomizing unit 30 includes an atomizing chamber 301, and a heating element 302 arranged in the atomizing chamber 301. The liquid tank 20 is configured (i.e., structured and arranged) for containing tobacco liquid. The second end 208 defines a liquid outlet 205. The tobacco liquid in the liquid tank 20 can flow into the atomizing chamber 301 via the liquid outlet 205. The heating element 302 is configured for heating tobacco liquid to form aerosol. The structures of the liquid tank 20 and the atomizing unit 30 will be described in detail below.

Figure 2:
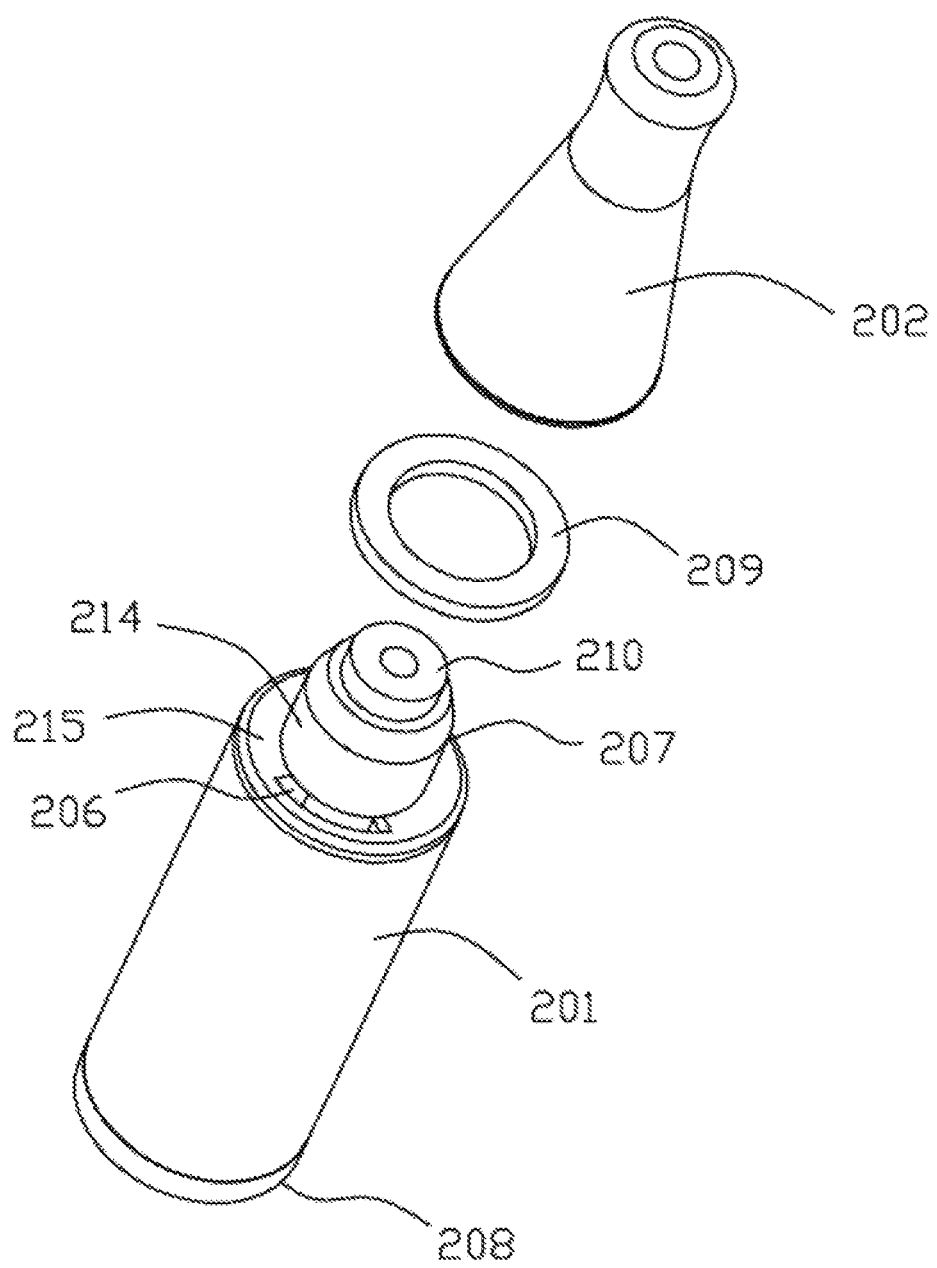
FIG. 2 is a perspective view of the liquid tank including a top part and a bottom part, when the top part is separated from the bottom part.

Referring to FIGS. 1-2, the liquid tank 20 is detachably connected to the atomizing unit 30. The liquid tank 20 includes a bottom part 201 and a top part 202. The bottom part 201 includes the first end 207 and the second end 208. The bottom part 201 defines a liquid chamber 204 adapted for storing tobacco liquid. The liquid outlet 205 is defined in the second end 208, and the second end 208 is configured for connecting with the atomizing unit 30. A first air inlet 206 is defined in the first end 207, so that external air can enter the liquid chamber 204. In the present liquid tank 20, the tobacco liquid flows out and the air flows in along different passages, and the tobacco liquid flows into the atomizing unit 30 smoothly due to gravity. Accordingly, a negative pressure will not be generated in the liquid tank 20, and the atomizer 10 is supplied with adequate tobacco liquid, thus enhancing efficiency of atomization.

The liquid tank 20 further includes a first porous liquid blocking element 209 covering the first air inlet 206. The first liquid blocking element 209 is configured for preventing the tobacco liquid in the liquid chamber 204 from leaking from the air outlet 206, and allowing air to pass through. When the tobacco liquid flows down via the liquid outlet 205, external air passes through a micro-hole structure of the first liquid blocking element 209 and enters the liquid chamber 204 via the first air inlet 206. Since the compactness of the first liquid blocking element 209 is high, liquid cannot pass through the first liquid blocking element 209. Accordingly, the tobacco liquid in the liquid chamber 204 is prevented from leaking via the first air inlet 206. The top part 202 is detachably connected to the first end 207. The top part 202 and the bottom part 201 cooperatively clamp the first liquid blocking element 209.

Quite usefully, the first liquid blocking element 209 is made of porous polyphenylene sulfone resins (PPSU) or cellucotton. When making the first liquid blocking element 209 using the PPSU, a foaming agent is added, and the PPSU is treated under a specific process to form a micro-hole structure, so that air can pass through the first liquid blocking element 209. By controlling a porosity of the PPSU, the liquid blocking element 209 can prevent tobacco liquid from passing through.

The top part 202 includes a hollow mouthpiece 203, through which the user can inhale aerosol. The mouthpiece 203 and a main body of the top part 202 are integrally formed. An air pipe 212 is provided in the liquid chamber 204. The air pipe 212 is in communication with the mouthpiece 203, thus forming an air passage 213. The air passage 213 mainly includes two parts: a first part defined in the air pipe 212 and a second part defined in the mouthpiece 203. The air passage 213 is in communication with the atomizing unit 30, so that the aerosol generated in the atomizing unit 30 flows out through the air passage 213, and is sucked via the mouthpiece 203.

Still further, a liquid absorbing component 210 is provided in the air passage 213 adjacent to the mouthpiece 203, and configured for absorbing liquid drops condensed in the air passage 213. The liquid absorbing component 210 defines a first through hole 211 extending axially. The first through hole 211 is in communication with the air passage 213, so that aerosol can pass through the first through hole 211. The liquid absorbing component 210 is made of porous material. The liquid absorbing component 210 may be made of porous PPSU, cellucotton, or cellulose acetate fiber.

Referring to FIG. 2, an engaging part 214 is provided on the first end 207, and configured for connecting with the top part 202. The engaging part 214 protrudes from the first end 207, and is hollow. The liquid absorbing component 210 is received in the engaging part 214. When the top part 202 is detached, the liquid absorbing component 210 can be replaced easily. The top part 202 is engaged with the engaging part 214 via interference fit. To fill the liquid chamber 204 with tobacco liquid, the top part 202 and the first liquid blocking element 209 may be detached, and the tobacco liquid may be filled via the first air inlet 206. It is to be understood that, the atomizing unit 30 may be detached, and the tobacco liquid may be filled via the liquid outlet 205.

The first end 207 further includes an annular stage 215. The first air inlet 206 is an annular sector, and is defined in the annular stage 215. The first liquid blocking element 209 is annular.

Figure 3:
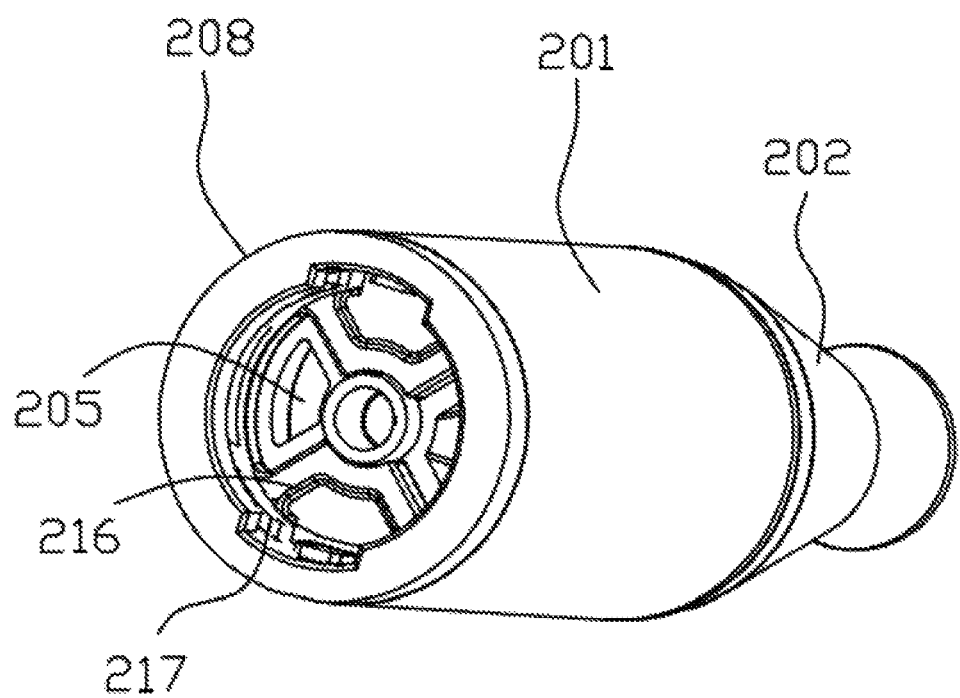
FIG. 3 is a perspective view of the liquid tank of FIG. 1.

Referring to FIG. 3, a rotatable sealing element 216 is provided at the second end 208 adjacent to the liquid outlet 205. The sealing element 216 is configured for sealing the liquid outlet 205, and defines a second through hole. When the second through hole is misaligned with the liquid outlet 205, the sealing element 216 seals the liquid outlet 205; when the second through hole is aligned with the liquid outlet 205, the liquid outlet 205 is opened. In the present embodiment, when the liquid tank 20 is in a natural state, the sealing element 216 is in a closed state. When the atomizing unit 30 is connected to the second end 208, the atomizing unit 30 drives the sealing element 216 to rotate to open the liquid outlet 205, and the atomizing unit 30 can work normally. The second end 208 further defines a recess 217 configured for coupling with the atomizing unit 30 to form a snap-fit connection.

Figure 4:
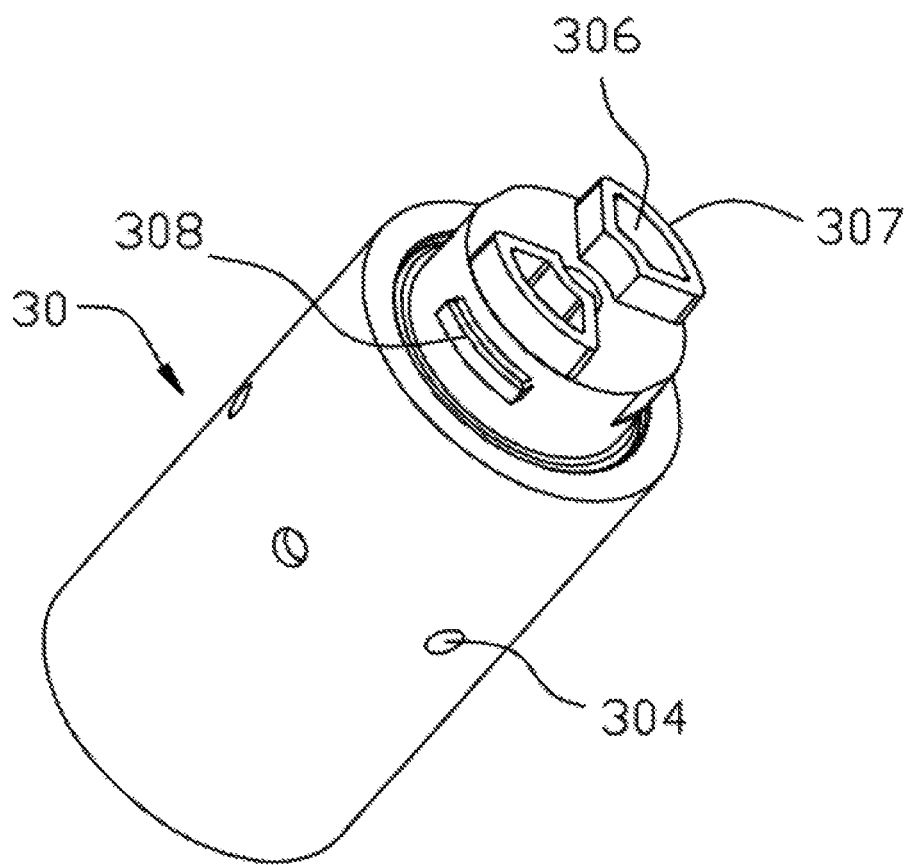
FIG. 4 is a perspective view of an atomizing unit of FIG. 1.
Figure 5:
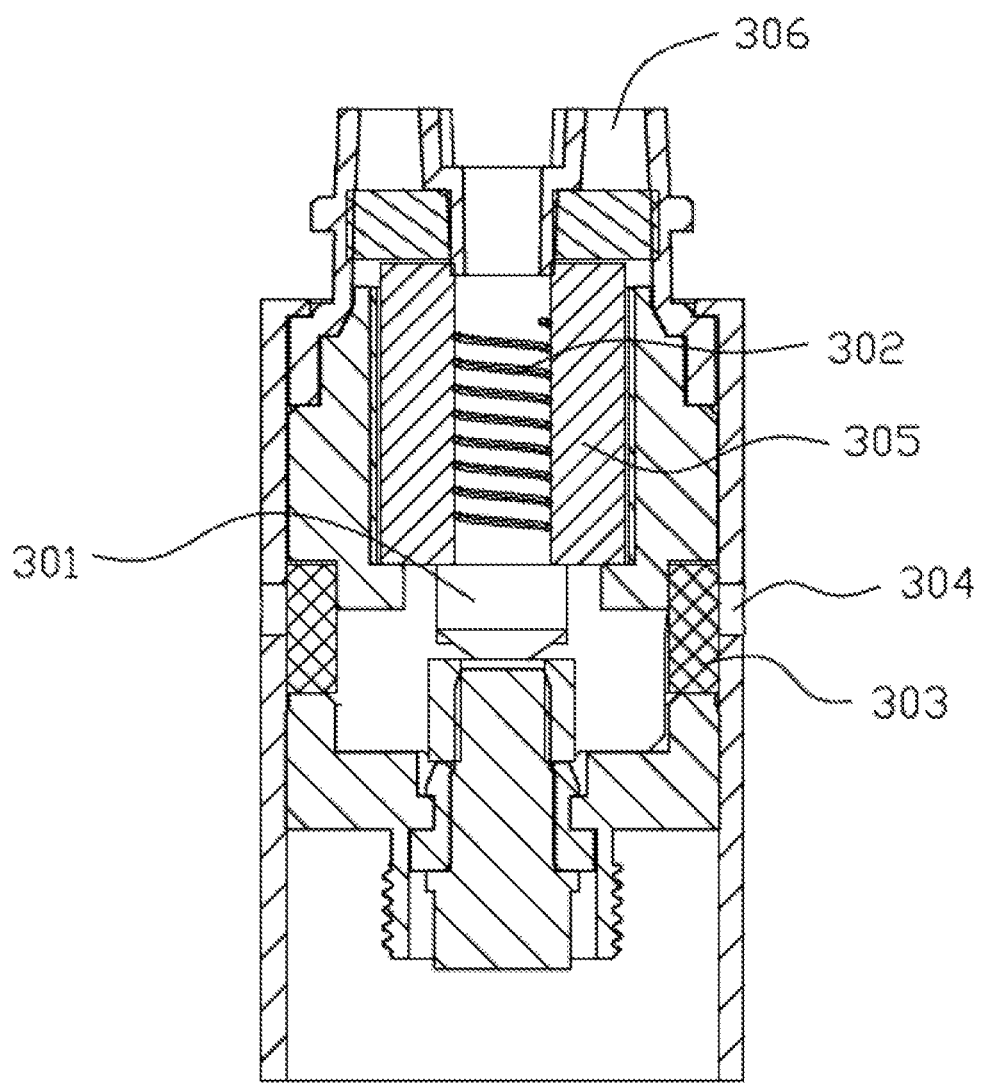
FIG. 5 is a cross-sectional view of the atomizing unit of FIG. 4.

Referring to FIGS. 4-5, the atomizing unit 30 is shown. The atomizing chamber 301 and the heating element 302 are arranged in the atomizing unit 30. Two protruding parts 307 are provided on an end of the atomizing unit 30 connecting with the second end 208. Each protruding part 307 defines a liquid inlet 306, which is selectively in communication with the liquid outlet 205. At least one latching part 308 is provided on a connecting end of the atomizing unit 30. The at least one latching part 308 is engaged in the recess 217 by rotating the atomizing unit 30, thus achieving a connection between the atomizing unit 30 and the liquid tank 20. During rotation, the protruding parts 307 are capable of driving the sealing element 216 to rotate, thus opening the liquid outlet 205. When the atomizing unit 30 is rotated to detach from the liquid tank 20, the protruding parts 307 are capable of driving the sealing element to rotate, thus sealing the liquid outlet 205.

A liquid absorbing cotton 305 is further provided in the atomizing chamber 301. In the present embodiment, the heating element 302 is a heating wire in a spiral form, and the liquid absorbing cotton surrounds the heating element 302. The liquid absorbing cotton 305 defines an aerosol passage extending through the liquid absorbing cotton 305. An end of the liquid absorbing cotton 305 is corresponding to the liquid inlet 306, so that the liquid absorbing cotton 305 can absorb tobacco liquid from the liquid inlet 306.

Quite usefully, the atomizing unit 30 defines a plurality of second air inlets 304 in a sidewall. The second air inlets 304 are evenly distributed along a circumferential direction of the atomizing unit 30. A porous second liquid blocking element 303 is provided between the second air inlets 304 and the atomizing chamber 301. The second liquid blocking element 303 is capable of preventing tobacco liquid stored in the atomizing chamber 301 from leaking, and allowing external air to pass through. Similar to the first liquid blocking element 209, the second liquid blocking element 303 may be made of porous PPSU or cellucotton. The second liquid blocking element 303 is annular, and seals the second air inlets 304, thus avoiding liquid leakage from the second air inlets 304.

Figure 6:
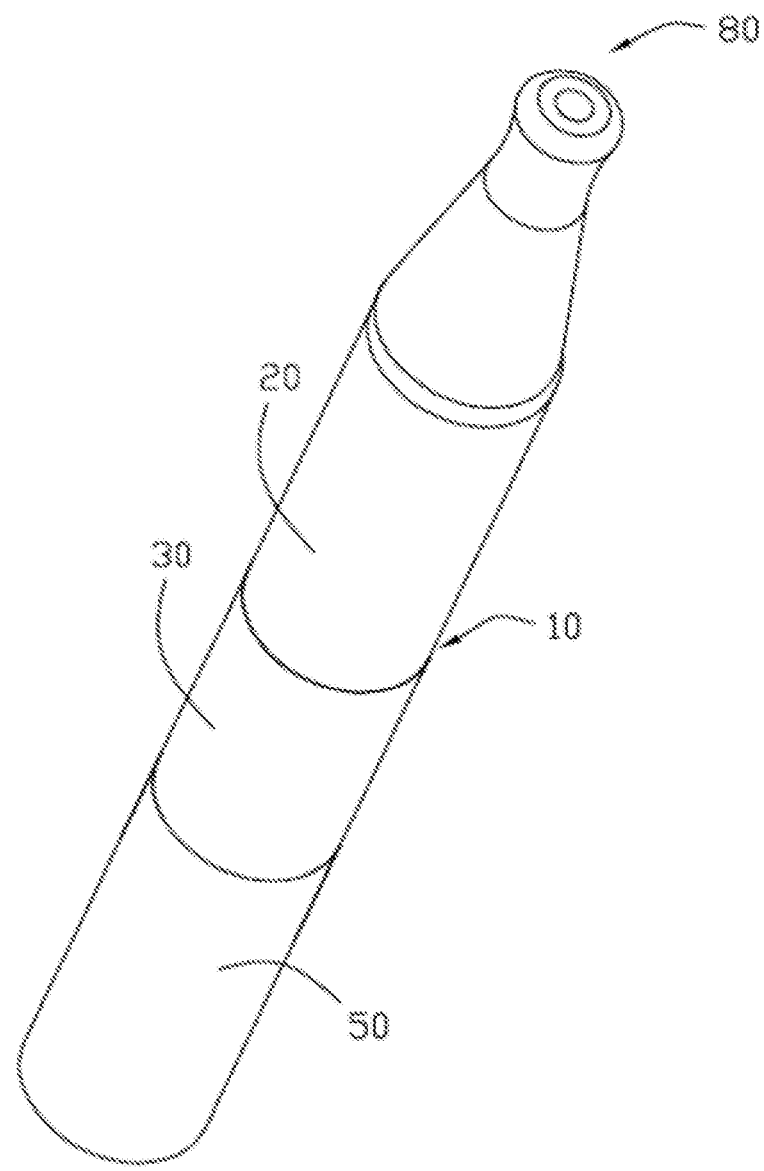
FIG. 6 is a perspective view of an electronic cigarette according to a second embodiment.

Referring to FIG. 6, the electronic cigarette 80 includes the above atomizer 10 and a power supply 50. The power supply 50 is connected to the atomizer 10, and configured for feeding the atomizer 10 power.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. A liquid tank for an atomizer, comprising:
   a bottom part having a first end and an opposite second end, the bottom part defining a liquid chamber for containing tobacco liquid;

a liquid outlet defined in the second end;

a first air inlet defined in the first end, so that external air can enter the liquid chamber via the first air inlet;

a first porous liquid blocking element covering the first air inlet, the first porous liquid blocking element being capable of preventing the tobacco liquid in the liquid chamber from flowing out via the first air inlet, and allowing air to pass through; and a top part detachably connected to the first end, the top part and the bottom part cooperatively clamping the first liquid blocking element therebetween.

2. The liquid tank according to claim 1, wherein the top part comprises a hollow mouthpiece.

3. The liquid tank according to claim 2, further comprising an air pipe arranged in the liquid chamber, wherein the air pipe is in communication with the mouthpiece, thus forming an air passage.

4. The liquid tank according to claim 3, further comprising a liquid absorbing component in the air passage adjacent to the mouthpiece, wherein the liquid absorbing component is configured for absorbing liquid drops condensed in the air passage, and the liquid absorbing component defines a first through hole extending axially.

5. The liquid tank according to claim 4, further comprising an engaging part on the first end, wherein the engaging part is configured for connecting with the top part, the engaging part is hollow, and the liquid absorbing component is received in the engaging part.

6. The liquid tank according to claim 1, wherein the first liquid blocking element is made of porous polyphenylene sulfone resins (PPSU) or cellucotton.

7. The liquid tank according to claim 1, further comprising an annular stage on the first end, wherein the first air inlet is an annular sector, and is defined in the annular stage.

8. An atomizer, comprising:

the liquid tank according to claim 1; and an atomizing unit connected to the second end of the bottom part, the atomizing unit comprising:

an atomizing chamber; and a heating element arranged in the atomizing chamber, wherein the tobacco liquid in the liquid tank flows into the atomizing chamber via the liquid outlet, and the heating element is configured for heating the tobacco liquid to form aerosol.

9. The atomizer according to claim 8, wherein the atomizing unit comprises a sidewall defining a plurality of second air inlets in communication with the atomizing chamber, the atomizer further comprises a porous second liquid blocking element provided between the second air inlets and the atomizing chamber, the second liquid blocking element is capable of preventing tobacco liquid stored in the atomizing chamber from leaking, and allowing external air to enter the atomizing chamber.

10. The atomizer according to claim 8, further comprising a rotatable sealing element arranged at the second end adjacent to the liquid outlet, wherein when the atomizing unit is connected to the second end, the atomizing unit is capable of driving the sealing element to rotate to open the liquid outlet.

11. An electronic cigarette, comprising:

the atomizer according to claim 8; and a power supply connected to the atomizer, the power supply being configured for supplying the atomizer power.

* * * * *